(12) United States Patent
Anitua Aldecoa

(10) Patent No.: US 8,936,467 B2
(45) Date of Patent: Jan. 20, 2015

(54) IMPLANT EXTRACTION METHOD AND TREPHINE DRILL BIT FOR ENABLING THE EXTRACTION

(75) Inventor: Eduardo Anitua Aldecoa, Vitoria (ES)

(73) Assignee: Biotechnology Institute, I Mas D, S.L., Vitoria (Alava) (ES)

( * ) Notice: Subject to any disclaimer, the term of this patent is extended or adjusted under 35 U.S.C. 154(b) by 17 days.

(21) Appl. No.: 13/044,799

(22) Filed: Mar. 10, 2011

(65) Prior Publication Data

US 2011/0223558 A1   Sep. 15, 2011

(30) Foreign Application Priority Data

Mar. 10, 2010  (ES) .................................. 201000307

(51) Int. Cl.
*A61C 3/00*    (2006.01)
*A61C 8/00*    (2006.01)
*A61C 3/02*    (2006.01)

(52) U.S. Cl.
CPC ........ *A61C 8/0089* (2013.01); *A61C 3/02* (2013.01)
USPC ............................. 433/152; 433/173; 433/215

(58) Field of Classification Search
USPC ........ 433/141, 152, 172–176, 201.1; 81/53.2, 81/120; 29/426.1, 426.5
See application file for complete search history.

(56) References Cited

U.S. PATENT DOCUMENTS

| | | | | |
|---|---|---|---|---|
| 2,488,036 A * | 11/1949 | Pofcher | .......................... | 433/152 |
| 4,807,349 A * | 2/1989 | Blackmore | .................. | 29/426.5 |
| 5,275,563 A * | 1/1994 | Cohen et al. | .................. | 433/224 |
| 6,761,089 B2 * | 7/2004 | Bergamo | ........................ | 81/53.2 |
| 7,179,084 B1 * | 2/2007 | Kometas | .......................... | 433/75 |
| 2009/0317771 A1 * | 12/2009 | Anitua Aldecoa | ............ | 433/215 |
| 2010/0081107 A1 * | 4/2010 | Bagambisa | ..................... | 433/75 |
| 2010/0126318 A1 | 5/2010 | Aldecoa | | |
| 2010/0304329 A1 * | 12/2010 | Heo | .............................. | 433/146 |

FOREIGN PATENT DOCUMENTS

WO   WO 2009153372 A2   12/1999

OTHER PUBLICATIONS

Comments Disabled to "Best Technique for Removing Osseointegrated Implant?", #2 Comment by Gary I. Henkel d.d.s., Jul. 17, 2007, OsseoNews.com Dental Implants, http://osseonews.com/best-technique-for-removing-osseointegrated-implants/.*
Ruedi et al. "AO Principles of Fracture Management", 2001. AO Publishing, vol. 1, p. 164.*

* cited by examiner

*Primary Examiner* — Edward Moran
(74) *Attorney, Agent, or Firm* — Browdy and Neimark, PLLC

(57) ABSTRACT

Method for extracting an implant installed in a bone, which comprises the application of a torque on an extraction tool in order to thread it in the interior of the implant until the implant-bone connection is broken, with the specific feature that the torque is applied in phases. In each phase a torque that is increasingly greater than in the previous phase is applied and the application of torque is then eased. This method brings about a gradual and controlled deformation of the head of the implant, with the result that the extraction tool is inserted more deeply into the implant. As a result, higher breakage torques may be applied without damage being caused to the extraction tool.

2 Claims, 4 Drawing Sheets

IMPLANT EXTRACTION METHOD AND TREPHINE DRILL BIT FOR ENABLING THE EXTRACTION

TECHNICAL FIELD

The invention relates to a method for extracting osseointegrated implants, and a design for a trephine drill bit that is especially suitable for executing said method.

PRIOR ART

Bone implants in general and dental implants in particular are biologically and mechanically designed to osseointegrate, in other words to join and fix themselves to the bone in a manner sufficiently strong for them to be able to withstand the high mechanical stresses the bone in which they are installed has to withstand. Because of this, the bone-implant connection in practice is very strong and is designed not to break easily.

Nevertheless, implants sometimes have to be removed from the bone in which they are osseointegrated (in the event of their incorrect installation or a change in the medical treatment of the area, etc). Generally speaking, the removal of an implant is a complex task due to the nature of the connection between the implant and the bone, which, as mentioned above, must be strong.

The removal of an osseointegrated implant is a process that can be somewhat traumatic for the bone and therefore for the patient. The traditional extraction procedure involves drilling with a hollow drill bit known as a 'trephine drill bit' around the implant. An area including the implant itself and a section of the surrounding bone is drilled. Once drilling is finished, the implant and said section of surrounding bone are removed. Unfortunately, this procedure leaves a cavity in the patient's bone that is larger than the cavity originally occupied by the implant, which is a negative factor as said cavity is usually too large for fitting another implant; because of this, a bone regeneration process is usually necessary in order to fill the cavity prior to continuing with the implant treatment.

The applicant recently designed a new tool for extracting implants, described in patent application WO2009153372, which enables dental implants to be extracted without the need to drill the bone around the implant. Said extraction tool comprises an external thread capable of being threaded into the blind hole of the implant, in an opposite direction to the external thread between the implant and the bone. The extraction procedure is based on threading the extraction tool inside the implant, by means of an additional torque application tool (e.g. the tool described in U.S. patent application Ser. No. 12/619079), slightly deforming the head of the implant. The extraction tool is threaded until the rotation torque is so high that the fastening between the extraction tool and the implant reaches its maximum point and said rotation torque is transferred to the implant-bone connection, eventually causing the breakage of the connection and the unthreading of the implant (or the simple breakage, in the event that the implant is not threaded to the bone). In order for this procedure to be executed, therefore, the extraction tool must be able to withstand high torques and to transfer said torques to the implant. Then, by means of the aforementioned extraction tool, the implant is removed cleanly, leaving behind it only the bone cavity occupied by the implant. As a result, there is no need to perform a subsequent bone regeneration phase, in addition to the fact that the process of extracting the implant is evidently made less traumatic for the patient.

It is an objective of this invention to provide an improved implant extraction method, based on the application of a high extraction torque on the implant, which is in turn transferred to the osseointegrated implant-bone connection. The method should make maximum use of the torque applied, with the result that it is not necessary to apply excessively high torques to bring about the breakage of said connection. The objective is that the surgeon should not have to exert a large amount of effort to break the implant-bone connection (as there is a risk of the extraction tool breaking under very high torques), and that, with the application of a specific maximum torque, stronger bone-implant connections may be broken than with the aforementioned method.

BRIEF DESCRIPTION OF THE INVENTION

It is an object of this invention to provide a method for extracting an implant installed in a bone, which comprises the application of torque on an extraction tool in order to thread it in the interior of the implant until the implant-bone connection breaks, with the specific feature that in said method the extraction torque is applied in successive phases. In each phase, an extraction torque is applied on the extraction tool until a specific maximum torque value is reached; the application of said torque is then eased. The specific maximum torque value increases in each successive phase. In other words, in the inventive method an increasing extraction torque is applied on the extraction tool until a specific maximum torque value is reached; the application of torque is then eased or stopped; an increasing extraction torque is applied once more up to a specific maximum torque value greater than the previous one; the application is eased once more, and so on until the connection between the implant and the bone is broken.

The method according to the invention, based on the gradual application of increasing torques in phases and with pauses, provides better results than the basic method described in WO2009153372, based on the application of an increasing extraction torque on the implant until, directly and without any pauses, the connection between the implant-bone is broken. It has been shown in testing that this method brings about a gradual and controlled deformation of the head of the implant, with the result that the extraction tool becomes more deeply inserted into the implant. The new effect is very important (in view of the fact that the extraction tool usually has a top part that increases in diameter) because the area of the extraction tool that withstands the stresses has a larger diameter and is therefore stronger, thereby enabling the application of higher breakage torques without damage being caused to the extraction tool.

DESCRIPTION OF THE DRAWINGS

Details of the invention can be seen in the accompanying non-limiting drawings.

DETAILED DESCRIPTION OF THE INVENTION

Figure 1:
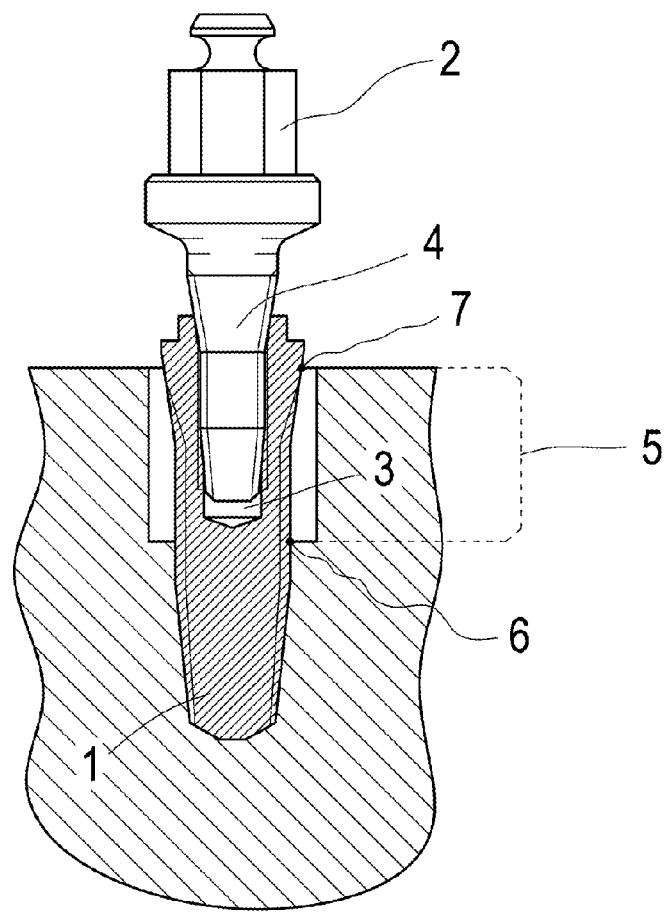
FIG. 1 shows a cross-sectional view of a dental implant and an extraction tool involved in the execution of the method according to the invention.

The invention relates to a method for extracting an implant installed in a bone, the method comprising the application of a torque on an extraction tool in order to thread it in the interior of the implant until the implant-bone connection breaks, with the specific feature that in said method the extraction torque is applied in successive phases. In each phase, an extraction torque is applied on the extraction tool until a specific maximum torque value is reached, and the application of said torque is then eased, said specific maximum torque value increasing in each successive phase. In other words, according to the inventive method, the extraction tool is placed inside the head of the implant and, by means of a torque-application tool, an increasing and gradual extraction torque is applied in the fastening direction of the extraction tool (generally in an anti-clockwise direction) until a first maximum torque value is reached. Said torque application tool is preferably an adjustable maximum torque wrench, such as the one described in U.S. patent application Ser. No. 12/619079. When this point is reached, the extraction tool is unthreaded, without it having to be removed completely. After it has been loosened and the inherent stresses in the extraction tool have been released, a torque is applied once more on the extraction tool until a second maximum torque value, greater than the previous one, is reached. This methodology is repeated, safeguarding the useful life of the extraction tool until the osseointegration between the implant and the bone is broken and the implant extracted.

Although the use of a multi-torque (adjustable) wrench or several fixed-torque wrenches of different values is preferable for carrying out the inventive method, the method may also be performed used a single fixed-torque wrench. In this respect dental professionals should use their judgement, which will help them decide the correct point at which the application of torque should be eased in each phase.

The method described herein enables the controlled deformation of the head of the implant as the extraction tool is threaded and, consequently, the deeper insertion of the extraction tool inside the implant. As a result, and given that the diameter of the extraction tool increases towards its apex, the area of the tool that applies the torque on the implant and withstands the stresses has a larger diameter (and is therefore stronger). In consequence, the extraction tool is capable of applying and withstanding higher torques. The surgeon is thus able break stronger implant-bone connections without breaking the extraction tool. In laboratory testing it has been shown that the inventive procedure allows torques up to 60% higher to be applied without the extraction tool breaking.

Preferably, the extraction method according to the invention comprises the additional step, in each phase (once the torque has been eased and before the application of a greater extraction torque in the next phase), of applying a torque in a direction opposite to the extraction direction in order to detach the extraction tool from the implant. This enables the extraction tool to enter further into the implant. As the extraction tool has a diameter that decreases towards its apex (in other words, a diameter that increases towards its top area), the fact that it is introduced further into the implant means that the active diameter of the extraction tool is increased. As a result, the strength of the connection between the extraction tool and the implant is increased considerably.

The inventive method optionally comprises the additional step of making in incision with a trephine drill bit in an external part of the implant-bone connection. The outermost area of the implant-bone connection is the area in which Bone-Implant Contact (BIC) is at its greatest. In fact, it has been estimated that when the implant has been installed in the bone for a considerable period of time, BIC in said outermost area may account for up to 80% of the total BIC between implant and bone. Trephining in this outermost area may thus result in a considerable reduction in the maximum torque that must be applied on the extraction tool.

FIG. 1 shows a cross-sectional view of an implant (1), in this case a dental implant, installed in a bone and to which an extraction tool (2) is connected. The extraction tool (2) is of the type that is used to perform the method according to the invention, thus comprising a threaded body (4) that is threaded into the blind threaded hole (3) of the implant (1). The threaded body (4) is inserted until it is so strongly threaded that the application of even greater torques on the extraction tool (2) causes the implant-bone connection to break.

As shown in the figure, in this case extraction is made easier by trephining on the outermost area (5) of the implant-bone connection. The trephining has two main effects. Firstly, it enables the point of application of the greatest stresses on the extraction tool (2) to be transferred to the implant (1), from the original point (7), without trephining, to the current point (6), which corresponds with an area of bone that is not as strong as that of the original point (7). Secondly, the stress on the current point (6), with trephining, is considerably greater than the stress on the original point (7), without trephining This effect may be seen in FIG. 6, which shows the stress applied on the bone in accordance with the depth of the point of application. As can be seen, when trephining is carried out for example up to a current point (6) at a depth of approximately 4.2 mm, the stresses applied to the bone from this point (the dashed line) have maximum values of approximately 200 MPa, whereas when trephining is not carried out the stress applied on the bone (the dotted line) has much lower maximum values, of 150 MPa, at the zero depth point (the original point (7) of FIG. 1). In other words, slight trephining of the outermost area (5) of the implant-bone connection causes a fitting effect that concentrates the stresses caused by the extraction tool (2) on the bone. The combination of both effects brings about a reduction in the maximum torque necessary to break the implant-bone connection.

Figures 2, 3:
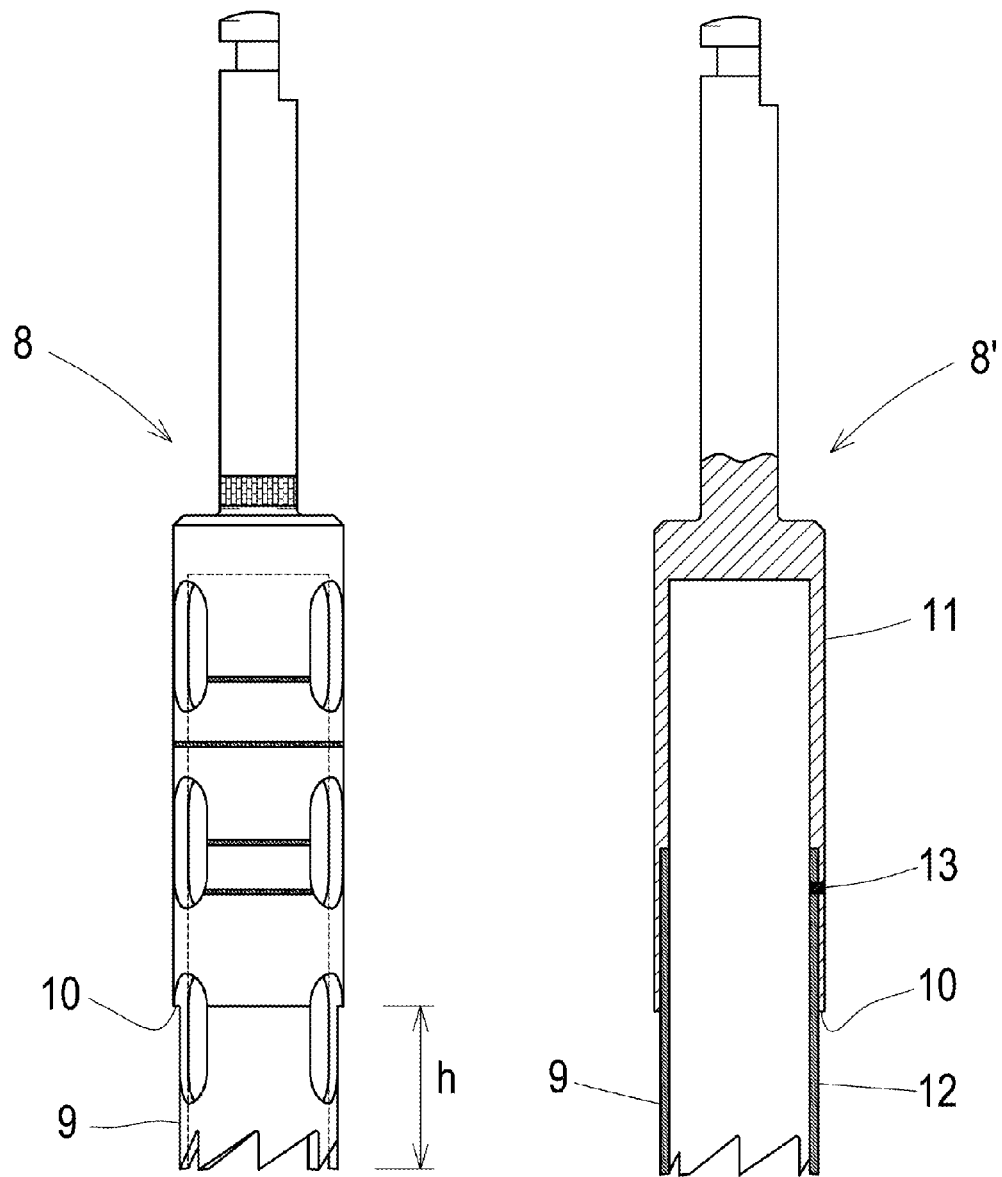
FIG. 2 shows an embodiment of the trephine drill bit according to the invention.
FIG. 3 shows a second embodiment of the trephine drill bit according to the invention.

FIG. 2 shows an elevated view of an embodiment of the trephine drill bit (8) according to the invention, which enables the trephining described above to be carried out safely and accurately on the outermost area (5) of the implant-bone connection. The outermost area of the trephine drill bit (8) comprises a reduced area (9) of a smaller diameter than the rest of the body of the trephine drill bit (8). Said reduced area (9) ends in a stop (10) that guides the surgeon during trephining and tells him/her when they have to insert the trephine drill bit (8). The stop (10) operates in such a way that, when the stop (10) comes into contact with the bone while trephining, the stop (10) does not cut or pull the bone but merely rubs against it. Because of the fact that the reduced area (9), i.e., the serrated cutting part on the end of the trephine drill bit (8), is especially thin and therefore requires a minimal amount of force for trephining, the rubbing of the stop (10) is enough to counteract said force. As a result, the rubbing of the stop (10) against the bone allows the surgeon to become aware that the trephine drill bit (8) has been inserted to the required limit Preferably, the height (h) of the reduced area (9) is between 2 and 8 mm An especially advantageous embodiment is that in which height is between 4.5 and 5.5 mm, in which the depth value of the trephining depth is optimised (in other words trephining is as brief but also as effective as possible in terms of the maximum torque reduction provided).

FIG. 3 shows a partial schematic cross-sectional view of a second embodiment of the trephine drill bit according to the invention. Here the trephine drill bit (8') comprises a body (11) and a tip (12), the latter being of a smaller diameter than the body (11) and being connected to it by means, for example, of a transverse fixing member (13), as shown in the figure. In this case, the reduced area (9) of the trephine drill bit (8') is on the tip (12) itself, while the end of the body (11) provides the stop (10). The advantage of this embodiment is that it allows a body (11) of one material (generally durable and not fragile) and a tip (12) of another material (generally hard) to be used.

Figure 4:
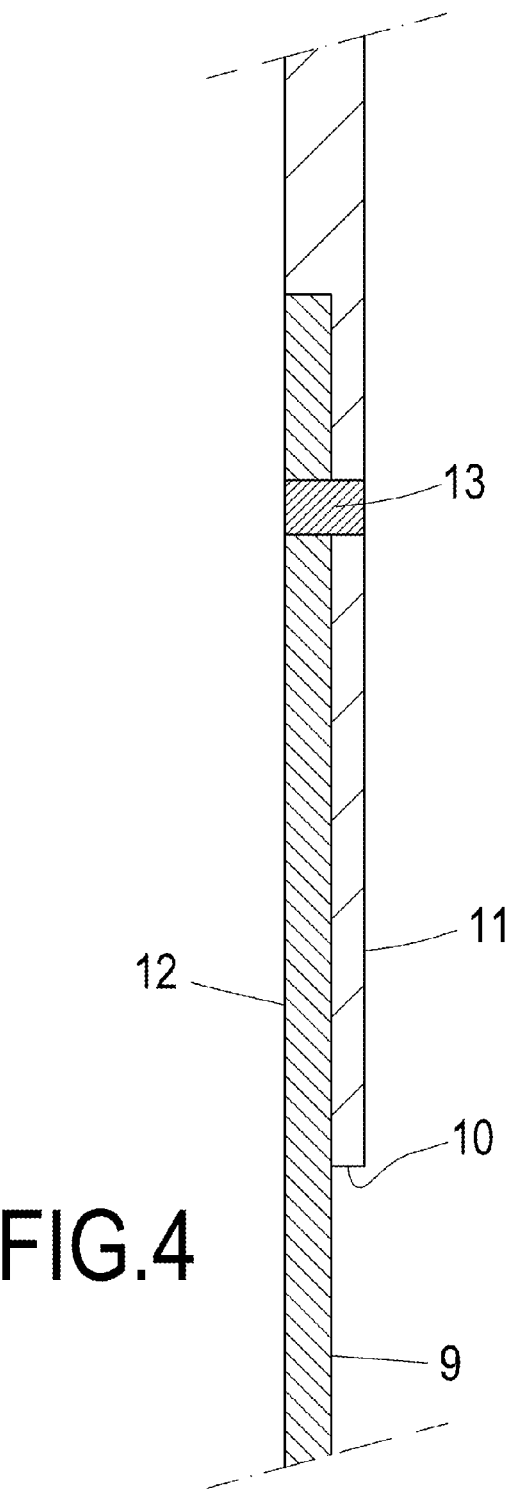
FIG. 4 shows an enlarged view of part of FIG. 3.

FIG. 4 shows an enlarged view of the area of FIG. 3 where the stop (10) is situated, more clearly illustrating all the aforementioned elements of the trephine drill bit (8').

Figure 5:
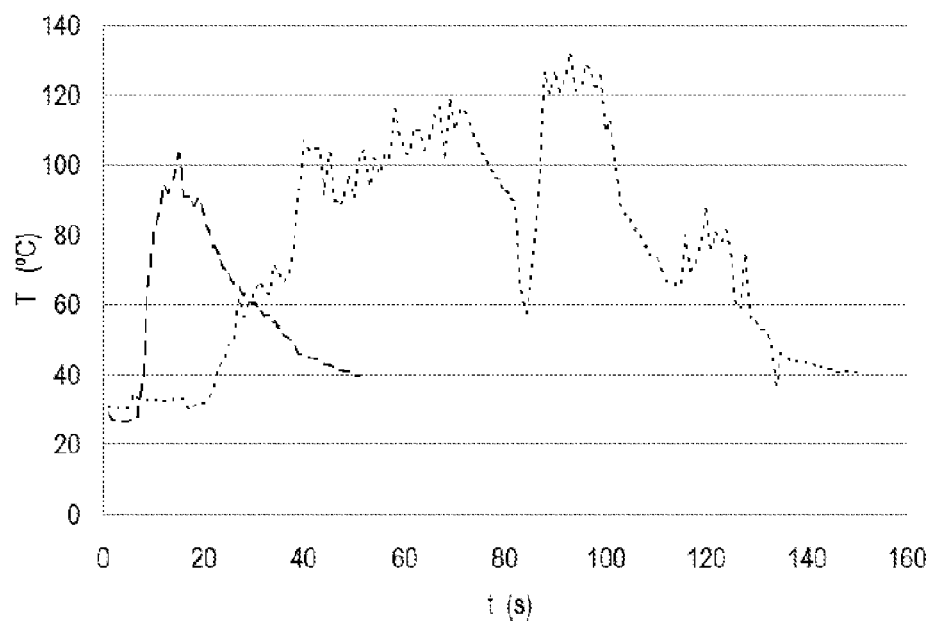
FIG. 5 shows a graph of the temperature the bone acquires with respect to the trephining time, the graph showing both the maximum temperature values generated using the trephine drill bit according to the invention and the maximum temperature values generated using a conventional trephine drill bit.

FIG. 5 shows a graph of the temperature the bone acquires in accordance with the trephining time, the maximum temperature values generated using the trephine drill bit according to the invention (dashed line) and a conventional trephine drill bit (dotted line) being compared. As can be seen, with the trephine drill bit according to the invention, which is used for drilling for a shorter period of time, the maximum temperature values acquired by the bone surrounding the trephine drill bit are lower throughout the trephining (lasting between 0 and 50 seconds in the case shown) in comparison to the maximum temperature values generated when trephining with a conventional trephine drill bit (a longer period of trephining lasting between 0 and 160 seconds). As a result, the use of the trephine drill bit according to the invention offers the additional advantage of preserving the quality of the bone surrounding the implant during the extraction.

The invention claimed is:

1. A method for extracting an implant installed in a bone comprising:
    a) inserting a threaded extraction tool having a tapered threaded body into an implant cavity;
    b) causing the threaded extraction tool to rotate and thread into the implant cavity, the threaded extraction tool meeting an increasing resistance to rotation originated by an increasing friction between the threaded extraction tool and inner walls of the implant cavity, whereby the threaded extraction tool is caused to rotate by applying an increasing torque on said tool in order to overcome said increasing resistance to rotation;
    c) ceasing rotation of the threaded extraction tool when said torque applied on the threaded extraction tool to produce rotation of said tool has reached a specific maximum torque value;
    d) partially unthreading said threaded extraction tool relative to the implant;
    e) and without removing said threaded extraction tool from the implant, carrying out a plurality of repetitions of steps b) through d), wherein in each execution of step c) a greater specific maximum torque value is reached than in the previous execution of step c), until an osseointegrated connection between said implant and the bone breaks, thereby allowing the implant to be removed.

2. The method according to claim 1, comprising the making of an incision with a trephine drill bit on an external part of the implant-bone connection in order to reduce the maximum torque that must be applied on the extraction tool.

* * * * *